(12) United States Patent
May

(10) Patent No.: US 6,657,198 B1
(45) Date of Patent: Dec. 2, 2003

(54) SYSTEM AND METHOD FOR WATER VAPOR DETECTION IN NATURAL GAS

(75) Inventor: Randy Dean May, Montrose, CA (US)

(73) Assignee: SpectraSensors, Inc., San Dimas, CA (US)

( * ) Notice: Subject to any disclaimer, the term of this patent is extended or adjusted under 35 U.S.C. 154(b) by 234 days.

(21) Appl. No.: 09/941,891

(22) Filed: Aug. 28, 2001

Related U.S. Application Data

(60) Provisional application No. 60/228,494, filed on Aug. 28, 2000.

(51) Int. Cl.[7] .............................................. G01N 21/01
(52) U.S. Cl. .............................. 250/339.13; 250/339.1; 250/338.5
(58) Field of Search ........................... 250/338.1, 338.5, 250/339.01, 339.06, 339.07, 339.1, 339.13

(56) References Cited

U.S. PATENT DOCUMENTS 5,107,118 A * 4/1992 Murray et al. ............... 250/339
6,064,488 A * 5/2000 Brand et al. ................. 356/440
6,292,756 B1 * 9/2001 Lievois et al. ................. 702/50

OTHER PUBLICATIONS

May, Computer Processing of Tunable Diode Laser Spectra, Applied Spectroscopy, 1989, pp. 834–839, vol. 43, No. 5.

May, "Open–path, Near–infrared Tunable Diode Laser Spectrometer for Atmospheric Measurements of H20", Journal of Geophysical Research, Aug. 20, 1998, pp. 19, 161–172, vol. 103, No. D15.

* cited by examiner

Primary Examiner—Constantine Hannaher
Assistant Examiner—Timothy Moran
(74) Attorney, Agent, or Firm—Carl A. Kukkonen, III

(57) ABSTRACT

A system and method are disclosed for the detection of water vapor in a natural gas background. The system includes a light source operating in the 1.877–1.901 μm wavelength range passes through the natural gas to be detected by a detector. In one embodiment, the light source is a tunable diode laser and the moisture level is determined by harmonic spectroscopy.

13 Claims, 3 Drawing Sheets

SYSTEM AND METHOD FOR WATER VAPOR DETECTION IN NATURAL GAS

This patent application claims the benefit of U.S. patent application Ser. No. 60/228,494, of Dr. Randy D. May, filed Aug. 28, 2000 which is hereby fully incorporated by reference.

BACKGROUND OF THE INVENTION

The present invention relates to a system and method for the detection of moisture in natural gas. More specifically, the present invention relates to a technique for determining the level of water vapor present within an industrial natural gas pipeline.

Natural gas has long been used as an energy source because of its low cost and widespread availability. After natural gas is mined, it is purified through several sequential processes, and distributed via networks of underground pipelines that typically transport the gas at a pipe pressure of several hundred pounds per square inch (PSI). Natural gas is sold to the customer as an energy product, and the energy content is generally expressed in British Thermal Units (BTU). The rate that gaseous product is pumped to the customer is measured in standard million cubic feet (SMCF), which is based on the gas volume at a standard pressure and temperature (typically 1 atmosphere pressure/14.73 PSI, and 70 degrees F.).

Contaminants in natural gas, such as water, reduce the BTU capacity of the gas, thereby resulting in a less efficient energy product. Contaminants also corrode delivery pipelines over time potentially resulting in serious safety hazards while also necessitating the costly replacement of segments of the pipeline (downtime for the pipelines can cost upwards of several thousand dollars per second). Accordingly, companies engaged in the mining, purification, and distribution of natural gas continuously monitor the quality of the gas at various stages of production and distribution to prevent such occurrences. One contaminant of particular interest is water vapor ($H_2O$). Excessive buildup of water vapor is a primary cause of pipeline corrosion, and it acts to dilute the natural gas thereby reducing its BTU capacity (thereby making the gas a less efficient energy source).

Distributors of natural gas typically have set maximum allowable levels of $H_2O$ within natural gas for various stages of natural gas production and distribution. The final product that is delivered to the customer (usually a large consumer supplier such as Southern California Gas, or Pacific Gas and Electric), is termed "mainline gas." The typical maximum allowable level of $H_2O$ in mainline gas is 7 lbs of $H_2O$ per measured million standard cubic feet of $CH_4$ (MMscf); 1 lb/MMscf is approximately 21.1 parts per million by volume, ppmv). This level is termed the "tariff". When $H_2O$ levels exceed tariff levels, plant operation can be suspended resulting in substantial loss of revenue and associated customer lawsuits.

Conventional techniques for measuring water vapor in natural gas rely primarily on the use of chemical sensors. These sensors operate by monitoring the capacitance or dielectric constant of a sensor element (made from compounds such as phosphorous pentoxide ($P_2O_5$) and aluminum oxide) subjected to a sample from the mainline gas. The electrical properties of the sensors change in a quantitative measurable manner as a function of the amount of water vapor present in the sample gas and such changes are translated into water concentration measurements. In such chemical sensors, a low pressure sample of pipeline gas is delivered to the sensor element via a regulation (pressure reduction) system. The gas sample measured by the pipeline is at a much lower pressure than the pipeline itself (typically 10–30 PSI, compared to 800 PSI in the pipeline). Such sensors are typically housed in sampling shelters that also house the accompanying regulation system.

As the sensing elements in chemical sensors are necessarily exposed to gas samples, contaminants in the gas stream such as glycols, amines, and oils directly contact the sensors. While chemical sensors can provide reliable measurements for short periods of time after calibration, the exposure to the contaminants (glycols and amines in particular) soil the sensor, thereby causing drifts in the calibration. This condition results in erroneous readings and can lead to eventual failure if the contaminants build up. Various filters (coalescing, adsorbents, and particle filters) have been employed to minimize the effects of glycol and amine contamination, but historically these filtration schemes are only temporary solutions. This is due in part because the filters are easily saturated with contaminants or they leak and require replacement at irregular intervals.

It should therefore be appreciated that there remains a need for a reliable and durable system and method for detection of water levels in natural gas.

SUMMARY OF THE INVENTION

The current invention utilizes absorption spectroscopy, a technique that has been utilized for decades to measure the concentration of water vapor in air, and in various laboratory environments. With such spectroscopy techniques, a light source is passed through a gas sample and detected by a detector opposite the light source. The light source can be a conventional hot filament, a glow bar, a laser, or any suitable emitter in the wavelength region of interest. By monitoring the amount of light absorbed by the sample, at specific wavelengths, the concentration of the target gas can be accurately determined.

A common problem with absorption spectroscopy is interference among constituents in the gas sample being measured. This interference occurs when the gas of interest (in this case $H_2O$) absorbs light at the same, or nearly the same, wavelength as another gas present in the sample. Natural gas, which is composed of >95% $CH_4$, has water vapor at typically less than 1% by volume. Conventional spectroscopic methods (i.e., non-laser based) are not suitable for measurements of $H_2O$ in a $CH_4$ background because the absorption by $CH_4$, which is present in much larger quantities, completely obscures the much weaker absorption by $H_2O$ at all wavelengths in the visible and infrared region.

The current invention operates in a wavelength range with minimal $CH_4$ absorption and preferably utilizes laser light sources for absorption spectroscopy, thereby minimizing the effects of interference due to the extremely high spectral purity of the laser (narrow line width). The current system incorporates a laser as its light source such as those used in automated, unattended, field instrumentation that operate at wavelengths between 1.6 and 2.7 microns ($\mu$m). The preferred lasers are the tunable diode lasers ("TDL") detailed in U.S. Pat. No. 5,257,256, which is hereby fully incorporated by reference. TDLs are widely utilized in optical communications, laser printers, bar code readers, CD players, and laser pointers. Alternatively, a color center laser which operates in the 1–3 $\mu$m region may be utilized, but such lasers are not always suitable for use in commercial field instrumentation due to their relatively large physical size, high power consumption, high maintenance requirements (they must be cryogenically cooled), and cost.

Laser-based measurements of water vapor in air use commercially-available TDLs operating at wavelengths near 1.38 µm, where water vapor has a strong absorption band. However, this wavelength is not suitable for measurements of $H_2O$ in a $CH_4$ background because $CH_4$ absorption in the 1.38 micron region is extremely strong and completely obscures absorption by $H_2O$ (see the spectrum of $CH_4$ in the 1–2 µm region 200 which is shown in FIG. 2).

The present system measures water vapor at another absorption band, 1.88 µm, where absorption by $CH_4$ is much weaker (see FIG. 3 which illustrates transmission spectra 300 (transmission=1−absorption) of $CH_4$ 325 and $H_2O$ 350 over wavenumbers 5260–5330 (wavenumber=1 µm, times 10,000)). There are several $H_2O$ absorption lines that can be used to monitor $H_2O$ in a natural gas background, but it is a wavelength range in the $CH_4$ absorption spectrum, 1.877–1.901 µm, that is preferred as it has strong $H_2O$ absorption lines, thereby allowing water vapor to be measured in a pure $CH_4$ background (see FIG. 4 which shows a spectrum 400 showing the relative positions of the $CH_4$ 425 and $H_2O$ 450 absorption lines over wavenumbers 5322–5336).

To improve detection sensitivity, the current system employs a technique called harmonic spectroscopy in connection with its TDL light source. Harmonic spectroscopy has been used since the 1950s in nuclear magnetic resonance spectrometers, stark spectrometers, and other various laboratory instruments. Harmonic spectroscopy as used in the current system involves the modulation of the TDL laser wavelength at a high frequency (kHz–MHz) and detecting the signal at a multiple of the modulation frequency. If detection is performed at twice the modulation, the term second harmonic spectroscopy is used. Advantages to this technique include the minimization of 1/f noise, and the removal of the sloping baseline that is present on TDL spectra (due to the fact that the laser output power increases as the laser injection current increases, and changing the laser injection current is how the laser is tuned).

Specifically, the present invention is embodied in a system for detecting water vapor in natural gas which includes a light source operating in the 1.877–1.901 µm wavelength range positioned to pass through the natural gas, a detector configured to receive light from the light source, and electronics coupled to the detector for computing the level of water vapor in the natural gas based on the amount of light detected by the detector. In some embodiments, the light source is a tunable diode laser, while in other embodiments, the light source is a color center laser. Furthermore, the detector is preferably an InGaAs detector.

The present invention is also embodied in a method for determining the level of water vapor in natural gas comprising the following steps: providing a light source emitting light in the wavelength range of 1.877–1.901 µm, positioning a detector opposite the light source to detect the level of emitted light, supplying a sample of natural gas between the light source and the detector, and determining the concentration of water vapor in the natural gas based on the level of light detected by the detector. In such a method, the gas is preferably taken by a gas line from a main pipeline into a shelter where the light source is housed.

Though the current system is described in connection with the sampling of natural gas from a main pipeline, it will be appreciated that the current system and method could be applied to any situation where it is desirable to measure the moisture content in natural gas or methane such as natural gas purification processes.

DESCRIPTION OF THE PREFERRED EMBODIMENTS

The current system and method relate to the measurement of moisture content in natural gas based on absorption of light at specific wavelengths where water molecule absorbs light strongly. Generally, this technique is referred to as absorption spectroscopy, and is applicable to the measurement of a wide range of gases, liquids, and solids.

Figure 1:
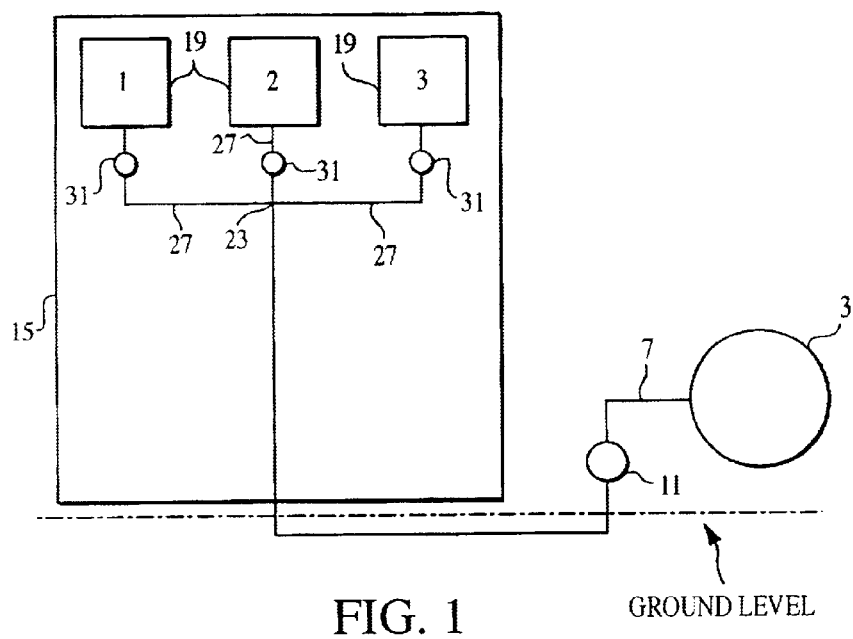
FIG. 1 is a block diagram of a conventional sampling shelter employing chemical sensors for the detection of contaminants in methane.
Figure 2:
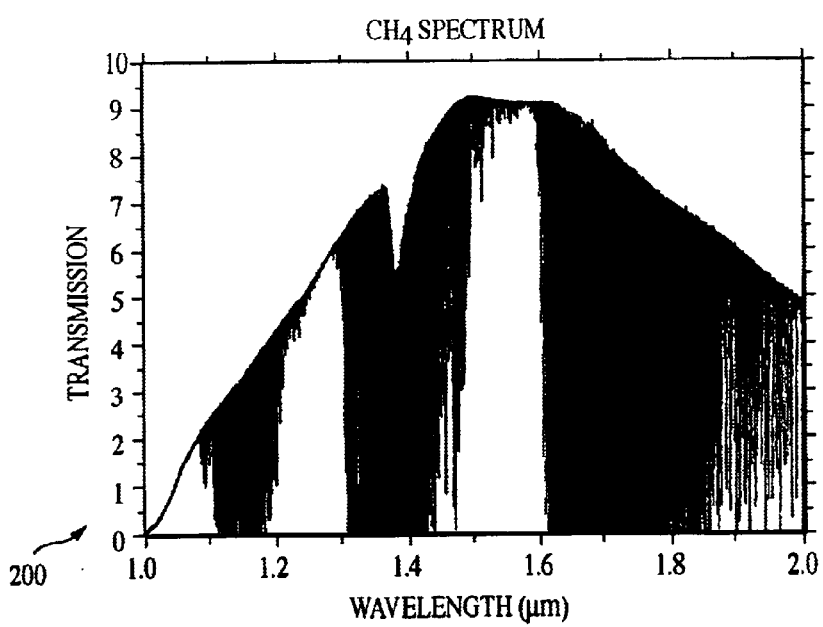
FIG. 2 is a spectrum of methane at wavelengths ranging from 1.0 µm to 2.0 µm.
Figure 3:
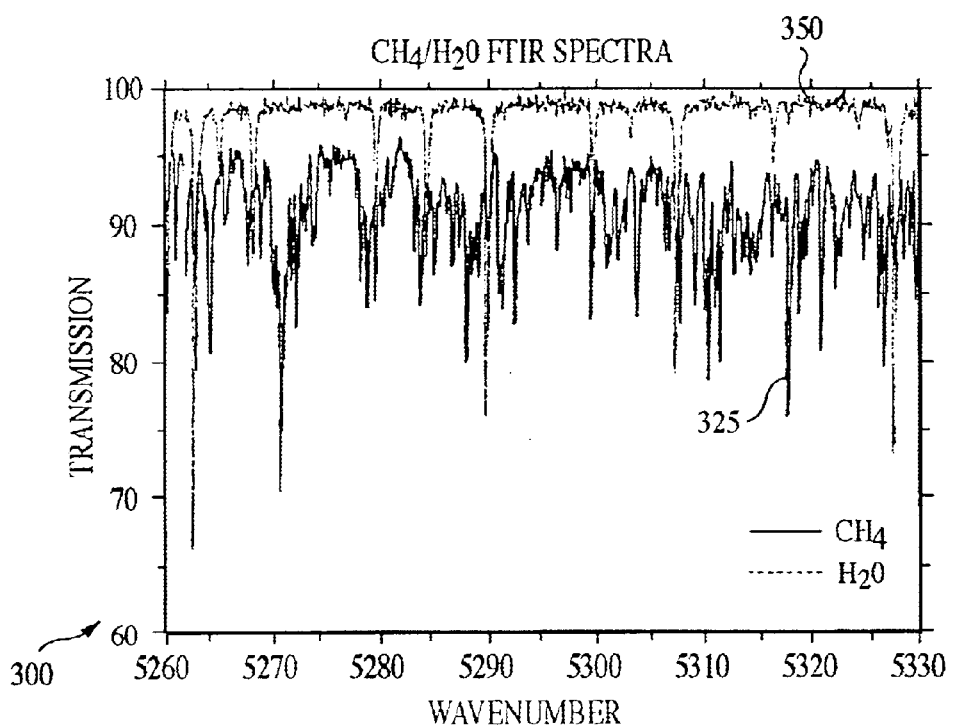
FIG. 3 is a spectrum of methane overlaid with a spectrum of water at wavenumbers ranging from 5260 to 5330.
Figure 4:
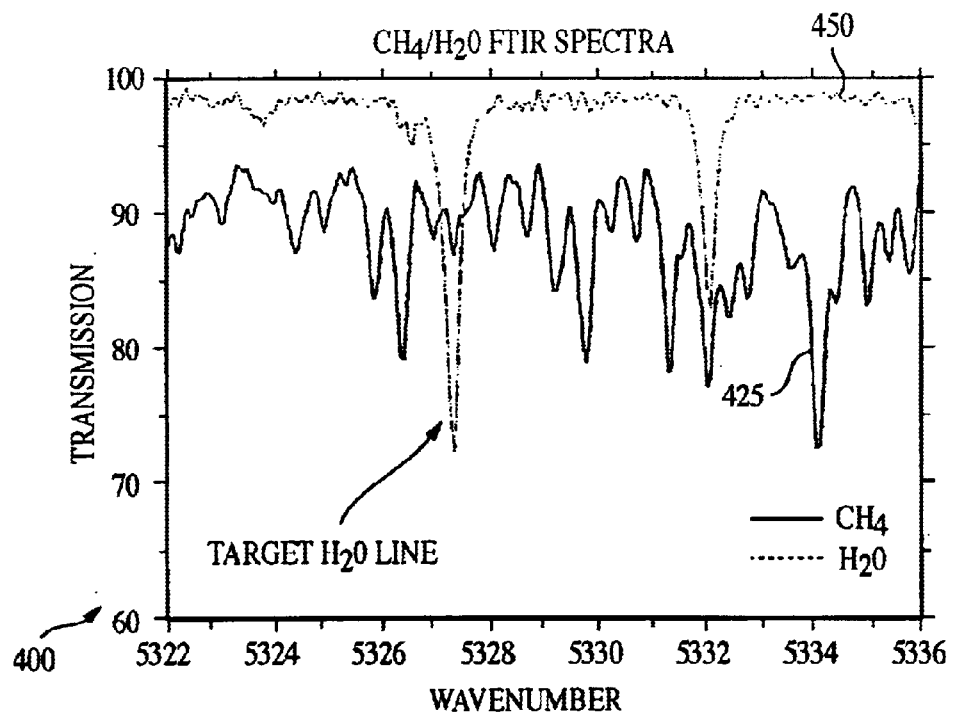
FIG. 4 is a spectrum of methane overlaid with a spectrum of water at wavenumbers ranging from 5322 to 5336.

As seen in FIG. 1, a pipeline 3 of natural gas is coupled to a gas line 7 which includes a regulator 11 for reducing the gas pressure within the gas line. From the regulator, the gas line enters a sampling shelter 15 that houses a plurality of sensors 19 (with at least one being an optical gas sensor as the present invention may be utilized in parallel with the chemical sensors described above). If multiple sensors are employed, they are connected in parallel to the gas line so that gas flow can be simultaneously directed to all of the sensors. This is accomplished after the gas line enters the sampling shelter by diverting gas into a plurality of feed lines 31 at juncture 23. Each of the feed lines are in turn coupled to a sensor and are controlled by a valve 27 to further restrict the flow of natural gas. Preferably, the gas line and the feed lines are made from stainless steel and have outer diameters of 0.25 inches.

Figure 5:
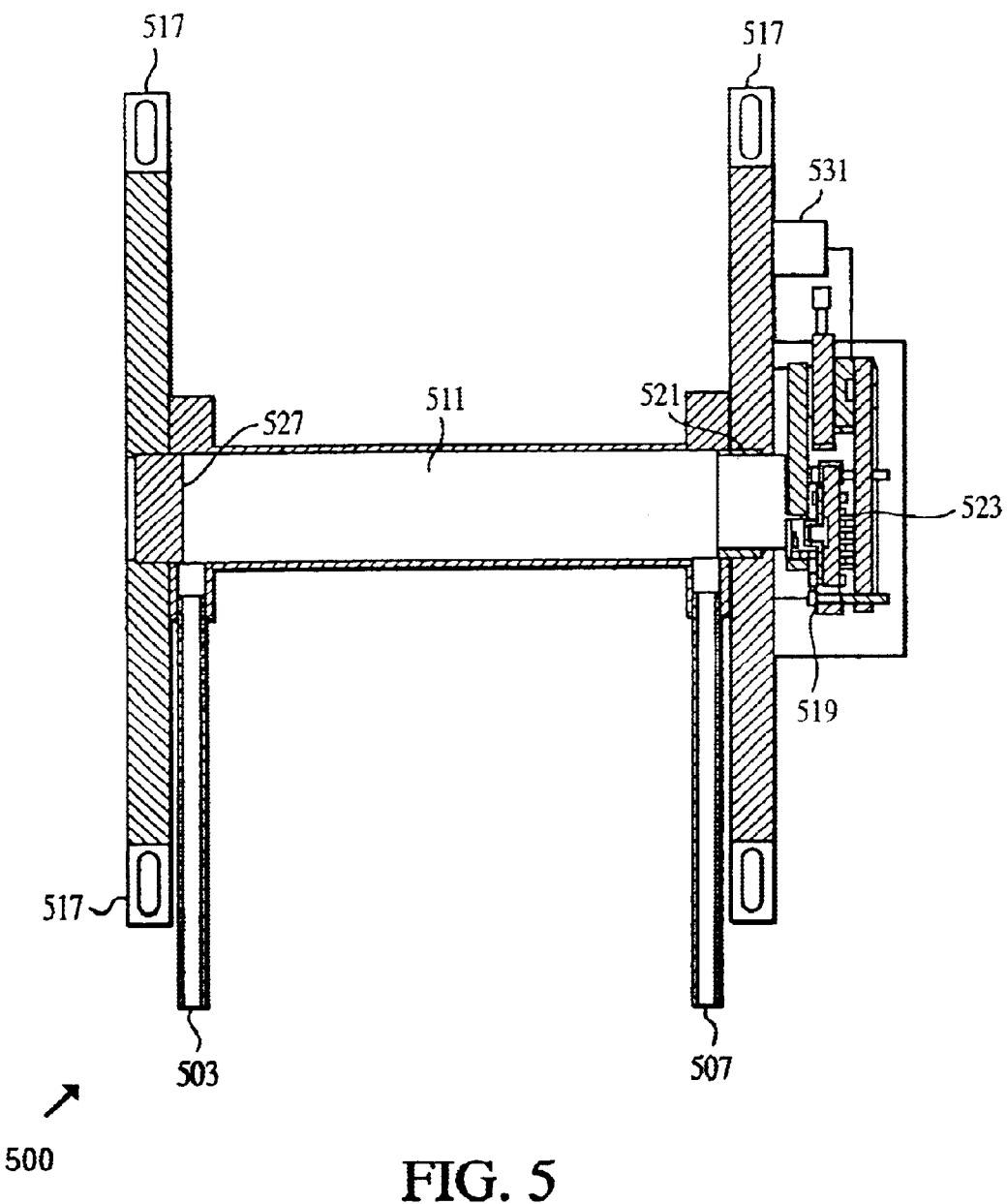
FIG. 5 is a cross-sectional view of the current invention for optically detecting water vapor within natural gas.

As seen in FIG. 5, a gas sensor 500 which is incorporated into the sampling shelter 15, includes an inlet 503, an outlet 507, and a light chamber 511, all of which are affixed within an optical gas sensor casing 515 (not shown) through a series of support flanges 517. The casing is configured to house a laser light source 519, an InGaAs detector adjacent to the light source 523, a window coupling the laser light source and the detector to the light chamber, a mirror opposite the laser light source 527, and processing electronics 531. The mirror is positioned preferably in such a manner to reflect light emitted from the light source through the light chamber and the window onto the detector. In one embodiment, the light source is positioned at 5 degrees from horizontal and the mirror is 40 cm from the light source. Preferably, the laser light source is a tunable diode laser configured to emit light in the 1.877–1.901 µm wavelength range. In one embodiment, the processing electronics includes a 16-bit Motorola microcontroller to convert the signals received by the detector into lbs per measured million cubic feet of methane (1 lb water/mmscf=21 ppm).

In operation, natural gas is fed into the inlet 503 of the gas sensor 500 to continually pass through the light chamber until it exits the gas sensor at the outlet 507. Thereafter, the processing electronics 531 are configured to translate the amount of light absorbed by the natural gas sample into water concentration using known techniques such as those described in article by Randy D. May et al. entitled "Processing and Calibration Unit for Tunable Diode Laser Harmonic Spectrometers", J. Quant. Spectrosc. Radiat. Transfer 49, 335–437, 1993, which is hereby incorporated by reference. Prior to coupling the gas sensor to the main gas line 7, it is preferred that a control sample of natural gas with a known concentration of water is passed through the gas sensor for calibration purposes.

It will be appreciated by one of ordinary skill in the art that standard techniques such as the incorporation of a Herriott cell to replace the single mirror configuration described above may be utilized to increase the effective optical path. For example, the Herriott cell could comprise two opposing Pyrex gold coated mirrors, each preferably with a radius of curvature of 150 mm and a diameter of 25.4 mm. In this embodiment, the tunable diode light source, is configured within the Herriot cell so that the emitted light bounces off each mirror approximately 15 times. This arrangement results in an effective travel path that is 30 times the length between the two mirrors for an effective distance of 4 meters. The light is then detected by the detector, which is coupled to electronics for converting the signals received into water concentration measurements. It should also be recognized that depending on the application, the number of reflections of the Herriott cell may be adjusted. For example, if the water vapor levels will be in the range of 5–100 lb/mmscf, then a single reflection system as described above should be utilized. If the concentration level will be within the range 0–5 lb/mmscf, then a Herriott cell should be utilized.

It will, of course, be understood that modifications to the preferred embodiments will be apparent to those skilled in the art. For example, different techniques may be used for supplying gas samples between the light source and the detector and for converting the signals received by the detector into concentration measurements. Consequently, the scope of the present invention should not be limited by the particular embodiments discussed above, but should be defined only by the claims set forth below and equivalents thereof.

What is claimed is:

1. A system for detecting water vapor in natural gas comprising:
    a light source emitting light at a frequency substantially corresponding to an absorption line of water in the 1.877–1.901 $\mu$m wavelength range, wherein said light source is positioned to emit light through the natural gas;
    a detector configured to detect the intensity of light emitted from said light source; and
    electronics coupled to said detector for determining the level of water vapor in the natural gas.

2. The system of claim 1 wherein said light source is a tunable diode laser.

3. The system of claim 1 wherein said light source is a color center laser.

4. The system of claim 1 wherein said detector is a InGaAs detector.

5. The system of claim 1 further comprising calibration means for calibrating the sensor relative to a known concentration of water vapor within the natural gas.

6. A method for determining the level of water vapor in natural gas, wherein the improvement comprises, using absorption spectroscopy to emit and detect light at a single absorption line of water in the wavelength range of 1.877–1.901 $\mu$m.

7. The method of claim 6 further comprising the following steps:
    providing a light source emitting light at a frequency substantially corresponding to a single water absorption line in the wavelength range of 1.877–1.901 $\mu$m;
    positioning a detector opposite the light source to detect the level of emitted light; and
    supplying a sample of natural gas between the light source and the detector; and
    determining the level of water vapor in the natural gas by the level of light detected by the detector.

8. A system for detecting water vapor in natural gas in a pipeline comprising:
    a sampling shelter;
    at least one optical gas sensor housed within said sampling shelter;
    a supply line coupled to the pipeline and said optical gas sensor for supplying natural gas to said optical gas sensor; and
    whereas said optical gas sensor comprises:
        a Herriott cell having two opposing mirrors;
        a tunable diode laser emitting light at a frequency within the 1.877–1.901 $\mu$m wavelength range substantially corresponding to a single water absorption line through said Herriott cell and configured to reflect off the mirrors to pass through the natural gas at least two times;
        a detector configured to detect the intensity of light emitted from said light source after the light reflects off the mirrors at least two times; and electronics coupled to said detector for determining the level of water vapor in the natural gas.

9. A system for detecting water vapor in natural gas comprising:
    a light source emitting light at a frequency approximately corresponding to a frequency where water molecules absorb light at a substantially greater level than natural gas molecules;
    a detector configured to detect the intensity of light from emitted from said light source; and
    electronics coupled to said detector for determining the level of water vapor in the natural gas and the level of water vapor in the natural gas.

10. The system of claim 9 wherein said light source is a tunable diode laser.

11. The system of claim 9 wherein said light source is a color center laser.

12. The system of claim 9 wherein said detector is an InGaAs detector.

13. The system of claim 9 further comprising calibration means for calibrating the sensor relative to a known concentration of water vapor within the natural gas.

* * * * *